US006664022B1

(12) United States Patent  
Cameron et al.

(10) Patent No.: US 6,664,022 B1
(45) Date of Patent: Dec. 16, 2003

(54) PHOTOACID GENERATORS AND PHOTORESISTS COMPRISING SAME

(75) Inventors: James F. Cameron, Cambridge, MA (US); Gerhard Pohlers, Newton, MA (US)

(73) Assignee: Shipley Company, L.L.C., Marlborough, MA (US)

( * ) Notice: Subject to any disclaimer, the term of this patent is extended or adjusted under 35 U.S.C. 154(b) by 0 days.

(21) Appl. No.: 09/648,022

(22) Filed: Aug. 25, 2000

(51) Int. Cl.$^7$ .............................................. G03F 7/004
(52) U.S. Cl. .................... 430/270.1; 430/325; 430/326; 430/914; 430/921; 430/922
(58) Field of Search ............................. 430/270.1, 914, 430/921, 922, 325, 326

(56) References Cited

U.S. PATENT DOCUMENTS

| | | | |
|---|---|---|---|
| 3,622,586 A | | 11/1971 | Zdravko |
| 3,763,187 A | * | 10/1973 | Moyle ...................... 260/332.3 |
| 3,896,140 A | | 7/1975 | Plepys et al. |
| 4,055,595 A | | 10/1977 | Haydock et al. |
| 4,087,554 A | * | 5/1978 | Haydock et al. ............ 424/353 |
| 4,090,936 A | * | 5/1978 | Barton ........................ 204/159 |
| 4,118,297 A | * | 10/1978 | Broxterman et al. ... 204/159.11 |
| 4,513,137 A | * | 4/1985 | Koser et al. ................... 546/14 |
| 5,932,391 A | | 8/1999 | Ushirogouchi et al. |
| 6,187,504 B1 | * | 2/2001 | Suwa et al. ............... 430/270.1 |
| 6,280,897 B1 | | 8/2001 | Asakawa et al. |
| 6,358,665 B1 | * | 3/2002 | Pawlowski et al. ....... 430/270.1 |
| 6,416,925 B1 | * | 7/2002 | Aoai et al. ................ 430/270.1 |

FOREIGN PATENT DOCUMENTS

| | | |
|---|---|---|
| EP | 0 789 278 | 8/1997 |
| EP | 0 846 681 | 6/1998 |
| EP | 0 849 634 | 6/1998 |
| EP | 0 972 761 | 1/2000 |
| GB | 2 340 830 | 3/2000 |
| JP | 09-304931 | * 11/1997 |
| WO | WO 00/10056 | 2/2000 |

OTHER PUBLICATIONS

Chemical Abstract 1970:54906.*
Chemical Abstract 1988:21404.*
Chemical Abstract 1993:233566.*
Chemical Abstract 1991:593968.*
Chemical Abstract 1999:453137.*
Chemical Abstract 1972:448122.*
Chemical Abstract 1997:206519.*
Chemical Abstract 1971:551455.*
Derwent Abstract of JP 09–304931, Nov. 1997.*
Chemical Abstract of JP 09–304931, Nov. 1997.*
Kitamura et al., Tetrahedron Letters, vol. 38, No. 29, 1997, pp. 5157–5160, CP002191800, Elsevier Science Publishers, Amsterdam., NL ISSN: 0040–4039, p. 5158.

Frohn et al., Journal of the Chemical Society, Chemical Communications, No. 10, 1989, pp. 625–627, XP002191801, Chemical Society. Letchworth., GB ISSN: 0022–4936, p. 627, Column 1; Table 1.
Kang et al., Journal of the Chemical Society, Chemical Communications, vol. 7, 1996, pp. 835–836, XP002191802, Chemical Society, Letchworth., GB ISSN: 0022–4936, p. 835, column1, line 32–line 35.
Moriarty et al., Tetrahedron Letters., vol. 28, No. 8, 1987, pp. 877–880, XP002191803, Elsevier Science Publishers, Amsterdam, NL, ISSN: 0040–4039.
Kitamura et al., Tetrahedron., vol. 49, No. 23, 1993, pp. 5055–5066, XP002191804, Elsevier Science Publishers, Amsterdam, NL, ISSN: 0040–4020, pp. 5063, line 40–line 46.
Beringer et al., Journal of the American Chemical Society, vol. 80, 1958, pp. 4279–4281, CP002191805, DC US p. 4280, column 2, line 55–line 56, p. 4281, column 2, line 6.
LaRochelle et al., Journal of the American Chemical Society, vol. 93, 1971, pp. 6077–6086, XP002191806, American Chemical Society, Washington, D.C., US, ISSN: 0002–7863, p. 6084, column 2, line 38–line 39.
Trost et al., Journal of the American Chemical Society, vol. 95, No. 16, 1973, pp. 5288–5298, XP002191807, American Chemical Society, Washington DC, US, ISSN: 0002–7863, Table III.
Margida et al., Journal of Organic Chemistry., vol. 49, No. 19, 1984, pp. 3643–3646, XP002191808, American Chemical Society, Easton., U.S., ISSN: 0022–3263, Table I.
Frohn et al., Journal of Fluorine Chemistry., vol. 64, No. 3, 1993, pp. 201–215, XP002191809, Elsevier Sequoia, Lausanne., CH, ISSN: 0022–1139, p. 210, line 17–line 18.
Gronowitz et al., Journal of Heterocyclic Chemistry., vol. 14, No. 2, 1977, pp. 281–288, XP002191810, Heterocorporation. PROVO., US, ISSN: 0022–152X, p. 285, column 2, paragraph 2.
Patent Abstracts of Japan, vol. 1995, No. 10, Nov. 30, 1995 & JP 07 179511 (Japan Carlit Co. Ltd: The), Jul. 18, 1995.
Chemical Abstracts, vol. 115, No. 4, Jul. 29, 1991, Columbus, Ohio, U.S.; abstract No. 30402t, Datatako et al., "Photochemically initiated cationic polymerization of ED–20 epoxy resin in presence of diphenyliodonium salts", p. 33, column 1, CP002191812, abstract & Kompoz. Polim. Mater., vol. 42, 1989, pp. 33–37.

(List continued on next page.)

Primary Examiner—Rosemary Ashton
(74) Attorney, Agent, or Firm—Peter F. Corless; Darryl P. Frickey; Edwards & Angell, LLP

(57) ABSTRACT

New photoacid generator compounds ("PAGs") are provided and photoresist compositions that comprise such compounds. In particular, ionic PAGs are provided that include tri-naphthyl sulfonium, thienyl iodonium, thienyl sulfonium, pentafluorophenyl iodonium and pentafluorophenyl sulfonium compounds. PAGs of the invention are particularly useful as photoactive components of photoresists imaged at short wavelengths such as sub-300 nm, sub-200 nm and sub-160 nm such as 248 nm, 193 nm and 157 nm.

26 Claims, No Drawings

OTHER PUBLICATIONS

Chemical Abstracts, vol. 84, No. 15, Apr. 12, 1976, Columbus, Ohio, US; abstract No. 100689j, Prows et al., "Development of a selective algaecide to control nuisance algal growth", p. 163; column 2; XP002191813, CAS RN 58506–52–8, abstract & U.S., Environ. Prot. Agency, Off. RS. Dev., 1973.

Stang et al., "Preparation of Bis(heteroaryl) Iodonium Salts Via an Iodonium Transfer Reaction Between Di(Cyano) Iodonium Triflate and Organostannes", Journal of Heterocyclic Chemistry, Heterocorporation. Provo, US, vol. 29, No. 4, 1992, pp. 815–818, XP002912907, ISSN: 0022–152X, p. 816, column 1, line 1–5.

Kitamura et al., Tetrahedron Letters, vol. 30, No. 52, 1989, pp. 7445–7446, XP002191811, Elsevier Science Publishers, Amsterdam., NL ISSN: 0040–4039.

Padelidakis et al., "Synthesis and characterization of 2,6–difluorophenyliodine(III) derivatives" Journal of Fluorine Chemistry, Elsevier Sequoia, Lausanne, CH, vol. 99, No. 1, Oct. 1999, pp. 9–15, XP004182984, ISSN: 0022–1139, Table 3.

Carroll et al., "New Synthesis of Diaryliodonium Sulfonates from Arylboronic Acids", Tetrahedron Letters, Elsevier Science Publishers, Amsterdam, NL, vol. 41, No. 28, Jul. 8, 2000, pp. 5393–5396, XP004222078, ISSN: 0040–4039, Tables 1,2.

Kitamura et al., "An Efficient Ligand Exchange Reaction of beta–(Trifyloxy)vinyliodonium Triflates with Aryllithium Reagents Leading to Diaryliodonium Triflates", Tetrahedron Letters, Elsevier Science Publishers, Amsterdam, NL, vol. 37, No. 21, May 2, 1996, pp. 3721–3722, XP004029242, ISSN: 0040–4039, Table 1.

Gallop et al., "Highly Effective PQQ Inhibition by Alkynyl and Aryl Mono– and Diiodonium Salts" Journal of the American Chemical Society, Ameican Chemical Society, Washington, DC, US, vol. 115, No. 25, 1993, pp. 11702–11704, XP002069912, ISSN: 0002–7863, p. 11703, column 1, line 1–line 5.

Miller et al., Journal of Organic Chemistry, American Chemical Society, Easton, US, Journal of Organic Chemistry, American Chemical Society, Easton, US., vol. 53, No. 23, 1988, pp. 5571–5573, XP002117748, ISSN: 0022–4263, Table 1.

* cited by examiner

PHOTOACID GENERATORS AND PHOTORESISTS COMPRISING SAME

BACKGROUND OF THE INVENTION

1. Field of the Invention

This invention relates to new photoacid generator compounds ("PAGs") and photoresist compositions that comprise such compounds. In particular, the invention relates to photoacid generator iodonium and sulfonium compounds having a cation component that comprises one or more substituents of naphthyl, thienyl or pentafluorophenyl. PAGs of the invention are preferably employed in resists imaged at short wavelengths, such as sub-300 nm and sub-200 nm, e.g. 248 nm, 193 nm and 157 nm, and ionzing radiation such as EUV, IPL, E-beam snd X-ray.

2. Background

Photoresists are photosensitive films for transfer of images to a substrate. They form negative or positive images. After coating a photoresist on a substrate, the coating is exposed through a patterned photomask to a source of activating energy such as ultraviolet light to form a latent image in the photoresist coating. The photomask has areas opaque and transparent to activating radiation that define an image desired to be transferred to the underlying substrate. A relief image is provided by development of the latent image pattern in the resist coating. The use of photoresists is generally described, for example, by Deforest, Photoresist Materials and Processes, McGraw Hill Book Company, New York (1975), and by Moreau, Semiconductor Lithography, Principals, Practices and Materials, Plenum Press, New York (1988).

Known photoresists can provide features having resolution and size sufficient for many existing commercial applications. However for many other applications, the need exists for new photoresists that can provide highly resolved images of submicron dimension.

Various attempts have been made to alter the make-up of photoresist compositions to improve performance of functional properties. Among other things, a variety of photoactive compounds have been reported for use in photoresist compositions. See, e.g., U.S. Pat. No. 4,450,360 and European Application 615163.

More recently, certain "chemically amplified" photoresist compositions have been reported. Such photoresists may be negative-acting or positive-acting and rely on multiple crosslinking events (in the case of a negative-acting resist) or deprotection reactions (in the case of a positive-acting resist) per unit of photogenerated acid. In other words, the photogenerated acid acts catalytically. In the case of positive chemically amplified resists, certain cationic photoinitiators have been used to induce cleavage of certain "blocking" groups pendant from a photoresist binder, or cleavage of certain groups that comprise a photoresist binder backbone. See, for example, U.S. Pat. Nos. 5,075,199; 4,968,851; 4,883,740; 4,810,613; and 4,491,628, and Canadian Patent Application 2,001,384. Upon selective cleavage of the blocking group through exposure of a coating layer of such a resist, a polar functional group is provided, e.g., carboxyl, phenol or imide, which results in different solubility characteristics in exposed and unexposed areas of the resist coating layer.

SUMMARY OF THE INVENTION

We have now discovered novel photoacid generator compounds (PAGs) for use in either positive-acting or negative-acting photoresist compositions.

We have found that excessive absorbance can remain an issue for resists imaged at short wavelengths such as 193 nm, even where the resist resin is optimized for low absorbance such as by having little or no aromatic content. In particular, we have found that a targeted absorption "budget" for a short wavelength resist may be substantially consumed by the resin component alone.

PAGs of the invention can exhibit good transparency to short wavelength radiation such as 193 nm. Accordingly, PAGs of the invention are particularly useful for photoresists imaged at short wavelengths such as 193 nm and 157 nm and can add minimal absorbance amounts to the formulated resist. PAGs of the invention are also useful for imaging at longer wavelengths such as 248 nm.

PAGs of the invention are sulfonium and iodonium compounds having a cation component that comprises one or more substituents of naphthyl, thienyl, or pentafluorophenyl, or a cation component that has a sulfur ring group such a thienyl, benzothiophenium, etc. Those substituents (chromophores) provide enhanced transparency of the PAG, while maintaining effective photoacid generation properties.

More particularly, in a first aspect of the invention, sulfonium and iodonium PAGs are provided that contain at least one naphthyl substituent, preferably multiple naphthyl substituents. Preferred naphthyl-substituted PAGs of the invention include sulfonium and iodonium compounds of the following Formulae I and II:

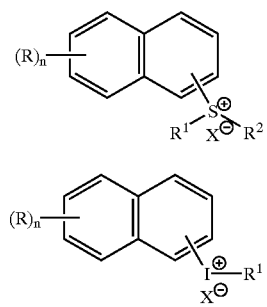

wherein in Formulae I and II: each R is the same or different non-hydrogen substituent such as hydroxy, cyano, nitro, halogen, optionally substituted alkyl including cycloalkyl; optionally substituted alkenyl; optionally substituted alkynyl; optionally substituted alkoxy; optionally substituted alkylthio; optionally substituted alkylsulfinyl; optionally substituted alkylsulfonyl; optionally substituted alkanoyl; optionally substituted carbocyclic aryl; or optionally substituted heteroalicyclic or heteroaromatic suitably having 1–3 rings with 3–8 ring members per ring and 1–3 $N_2$ O or S atoms;

each n is an integer equal to 0 (where the naphthyl group has no non-hydrogen substituents) to 7, more typically 0, 1, 2, 3 or 4; and $R^1$ and $R^2$ are the same or different and each is suitably an aromatic or non-aromatic group such as e.g. optionally substituted alkyl including cycloalkyl; optionally substituted alkenyl; optionally substituted alkynyl; optionally substituted alkoxy; optionally substituted alkylthio; optionally substituted alkylsulfinyl; optionally substituted alkylsulfonyl; optionally substituted carbocyclic aryl; or optionally substituted heteroalicyclic or heteroaromatic suitably having 1–3 rings with 3–8 ring members per ring and 1–3 N, O or S atoms, with aromatic groups typically being preferred $R^1$ groups;

X is a counter anion, particularly an organic anion such as a sulfonate e.g. of the formula R'SO$_3$ where R' is suitably optionally substituted alkyl, particularly perfluoroalkyl typically having 1 to about 12 carbon atoms such as triflate and the like; carbocyclic aryl such as pentafluorophenylsulfonate; and the like; or X is suitably a carboxylate, e.g. groups of the formula R"COO— where R" is optionally substituted alkyl having 1 to about 18 carbons or optionally substituted aryl such as phenyl and the like. Preferred substituents of substituted carboxylate anions include halo, particularly fluoro.

Particularly preferred compounds of the above formulae are those that have multiple naphthyl groups, such as compounds of the following Formulae IA, IB, and IIA:

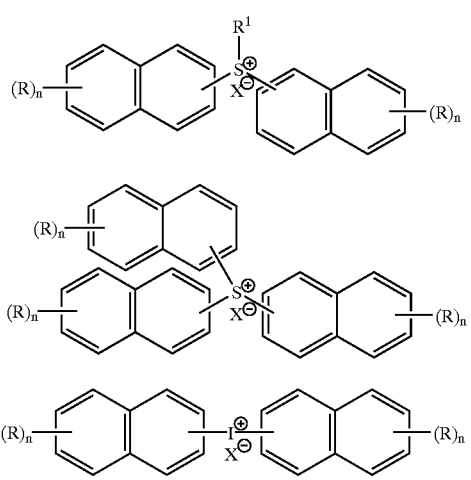

wherein in each of Formula IA, IB and IIA, R, n, R1 and X are the same as defined for Formulae I and II above.

In Formulae I and II, IA, IB and IIA, a naphthyl group may be linked to the iodonium or sulfonium cation at either the 1- or 2-naphthyl positions.

In a further aspect, sulfonium and iodonium PAGs are provided that contain at least one thienyl substituent. Preferred thienyl-substituted PAGs of the invention include sulfonium and iodonium compounds of the following Formulae III and IV:

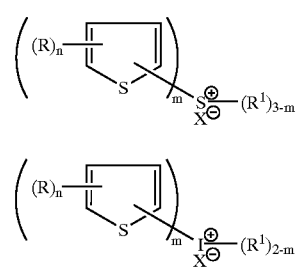

wherein in Formulae III and IV: R, R$^1$ and X are the same as defined in Formula I and II above;

in Formula III, m is 1, 2 or 3;

in Formula IV, m is 1 or 2; and each n is an integer equal to 0 (where the thienyl group has no non-hydrogen substituents), 1, 2 or 3, preferably 0, 1 or 2.

Preferred PAGs of Formulae III and IV include compounds that have multiple thienyl substituents, such as compounds of the following Formulae IIIA, IIIB, and IVA:

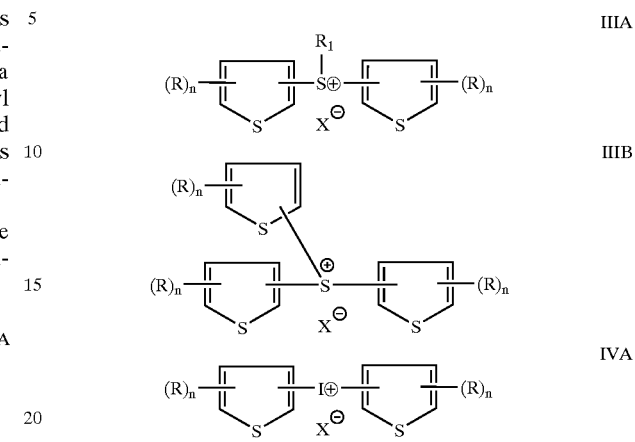

wherein in Formulae IIIA, IIIB and IVA: each R, R$^1$, n and X is the same as defined for Formnulae III and IV above.

In Formulae III, IV, IIIA, IIIB and IVA a thienyl group may be linked to the iodonium atom or sulfonium atom at the 2- or 3-thienyl ring positions.

In a further aspect, sulfonium and iodonium PAGs are provided that contain at least one pentafluorophenyl substituent. Preferred pentafluorophenyl-substituted PAGs of the invention include sulfonium and iodonium compounds of the following Formulae V and VI:

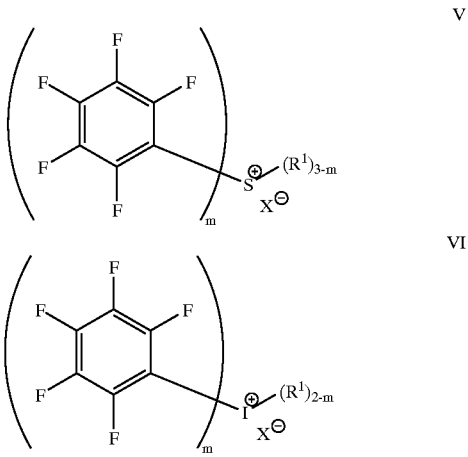

wherein in Formula V and VI: R$^1$ and X are the same as defined in Formulae I and II above;

in Formula V, m is 1, 2 or 3; and in Formula VI, m is 1 or 2.

Preferred PAGs of Formula V and VI include those that have multiple pentafluorophenyl groups, such as compounds of the following Formulae VA, VB and VIA:

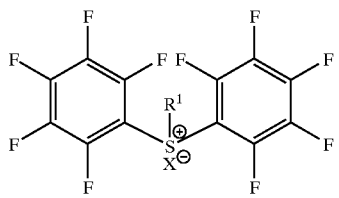

VA

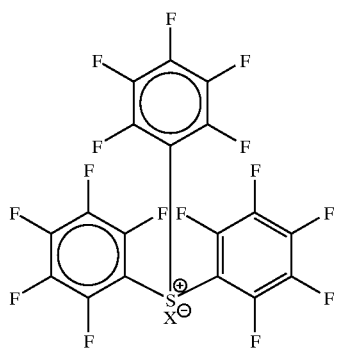

VB

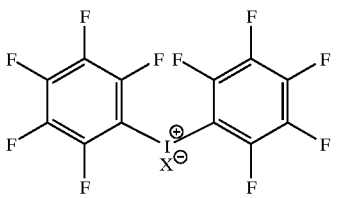

VIA wherein in Formulae VA, VB and VIA: $R^1$ and X are the same as defined in Formulae I and II.

Preferred PAGs of the invention also include sulfonium and iodonium PAGs that contain at least two distinct substituents selected from the group consisting of naphthyl, thienyl and pentafluorophenyl, such as compounds of the following Formulae VII and VIII:

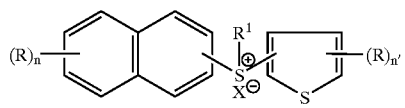

VII

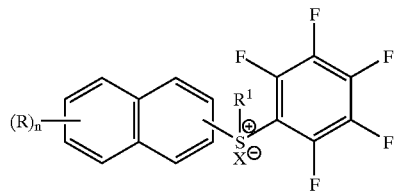

VIII

IX

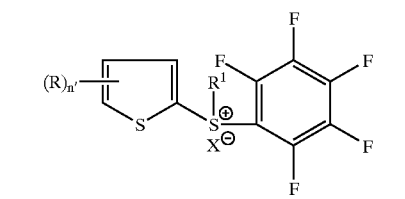

X

XI

XII wherein in Formulae VII, VIII, IX, X, XI and XII: R, $R^1$, n and X are the same as defined in Formulae I and II above; and n' is an integer equal to 0 (where the thienyl group has no non-hydrogen substituents), 1, 2 or 3, preferably 0, 1 or 2.

Preferred $R^1$ groups of Formulae VII, VIII and IX include pentafluorophenyl, optionally substituted thienyl and optionally substituted naphthyl.

As discussed-above, preferred PAGs of the invention include sulfonium compounds where the sulfur cation is a ring member, e.g. a member of a ring having 5 to about 25 atoms (typically carbon) and 1 to 3 or 4 separate or fused rings. Thienyl rings are generally preferred, suitably optionally substituted, which substitutions can include one or more aromatic or alicyclic rings fused or otherwise linked to the thienyl ring.

Such preferred ring sulfonium cation PAGs include those of the following Formula XIII:

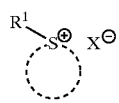

XIII where $R^1$ and X are the same as defined in Formula I above; the dotted lines designate a ring structure that includes the depicted sulfur cation as a ring member, the ring suitably having 5 to about 8 ring members, and one, two or more endocyclic multiple bonds, and one or more optional substituents, including additional ring substituents such as a phenyl or naphthyl that would linked by a single bond or fused to the sulfur cation-ring.

Generally preferred are compounds where the sulfur cation is a member of a thienyl-based ring system, such as PAGs of the following Formula XIV:

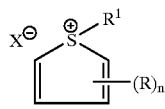

XIV wherein R, R¹, X and n are each the same as defined in Formula I above, and further where two R groups typically on adjacent ring atoms may together form a fused alicyclic or aromatic ring suitably having 5 to about 8 ring members such as optionally substituted phenyl (e.g. to provide a benzothiophenium group) or optionally substituted naphthyl fused to the thienyl group.

In each of the above formulae, preferably two hetero atoms (N, O or S) are not adjacent to each other. Thus for example, in Formulae I and II, if an R¹ substituent is alkoxy, preferably the oxygen of the alkoxy is not directly linked to the S⁺ (Formula I) or I⁺ (Formula II) atoms; rather, at least a single carbon spacer (e.g. —CH₂—) will be interposed between the S⁺ or I⁺ atoms and the oxygen of the alkoxy linkage.

Preferred R groups of compounds of Formulae I, II, IA, IB, IIA, III, IV, IIA, IIIB, IVA, VII, VIII, IX, X, XI, XII, XIII and XIV include hydroxy; halogen, particularly F, Cl or Br; optionally substituted $C_{1-6}$alkoxy such as methoxy and ethoxy, $C_{1-6}$alkyl such as methyl, ethyl and perfluoroalkyl such as trifluoromethyl, pentafluoroethyl, etc.

Preferred R¹ and R² groups of compounds of Formulae I, II, IA, III, IV, IIIA, V, VI, VII, VIII, IX, XIII and XIV include cyclic groups, particularly aromatic groups such as optionally substituted carbocyclic aryl such as phenyl, and substituted phenyl such as halo-phenyl preferably pentafluorophenyl, naphthyl and the like; and heteroaromatic groups such as thienyl and the like. Carbon alicyclic and heteroalicyclic groups also will be suitable R¹ and ² groups such as adamantyl, fenchyl and the like.

Generally preferred X anion groups of compounds of the above formulae are organic anions, including sulfonate and carboxylate anions. Preferred sulfonate X anion groups include those of the formula R'SO₃ where R' is suitably optionally substituted alkyl, particularly perfluoroalkyl typically having 1 to about 12 carbon atoms such as triflate and the like; carbocyclic aryl such as pentafluorophenyl sulfonate; and the like. Preferred carboxylate X groups include those of the formula R"COO— where R" is optionally substituted alkyl having 1 to about 18 carbons or optionally substituted aryl such as phenyl and the like. Preferred substituents of substituted carboxylate anions include halo, particularly fluoro.

Other suitable anion X groups include arsenic anions such as halogenated compounds e.g. $AsF_6^-$; phosphonium compounds such as halogenated P compounds, e.g. $PF_6^-$; and borates such as halo, alkyl and/or aryl substituted borate compounds, e.g. $B(C_6H_5)_4^-$ and $BF_4^-$.

Specifically preferred counter anions of PAG compounds of the invention (group X in above formulae) include:
  2-acrylamido-2-methyl-1-propanesulfonate;
  8-anilino-1-naphthalenesulfonate;
  benzylsulfonate;
  t-butanesulfonate;
  4-t-butylbenzenesulfonate;
  camphorsulfonate;
  di-(2-ethylhexyl)succinatesulfonate;
  2,6-difluorobenzoate;
  3,4-dimethoxybenzenesulfonate;
  5-dimethylamino-1-naphthalenesulfonate;
  3-(4-dimethylamino-1-naphthylazo)-4-methoxybenzenesulfonate;
  4-[(4-dimethylamino)phenylazo]benzenesulfonate;
  2,4-dinitrobenzenesulfonate;
  (2-/3-/4-)-dodecylbenzenesulfonate;
  ethanesulfonate;
  4-fluorobenzenesulfonate;
  hexadecanesulfonate;
  hexa fluorophosphate;
  methanesulfonate;
  1-naphthalenesulfonate;
  2-naphthalenesulfonate;
  4-octylbenzenesulfonate;
  pentafluorobenzenesulfonate;
  pentamethylbenzenesulfonate;
  4-pyridineethanesulfonate;
  3-pyridinesulfonate;
  thymol blue;
  toluenesulfonate;
  2,4,5-trichlorobenzenesulfonate;
  2,2,2-trifluoroethanesulfonate;
  trifluoromethanesulfonate (triflate);
  trifluoroacetate;
  2-trifluoromethylbenzenesulfonate;
  3-trifluoromethylbenzenesulfonate;
  4-trifluoromethylbenzenesulfonate;
  3,5-bis(trifluoromethyl)benzenesulfonate;
  2,4,6-triisopropylbenzenesulfonate;
  2,4,6-trimethylbenzenesulfonate;
  perfluoroctanesulfonate;
  perfluorohexanesulfonate;
  perfluorobutanesulfonate; and
  perfluoroethoxyethylsulfonate.

Of the above, the perfluoroalkyl and perfluoroalkoxy anions are often preferred such as triflate; perfluorobutanesulfonate; perfluorhexanesulfonate; perfluorooctanesulfonate; and perfluoroethoxyethylsulfonate.

Preferably, PAGs of the invention are used in positive-acting or negative-acting chemically amplified photoresists, i.e. negative-acting resist compositions which undergo a photoacid-promoted crosslinking reaction to render exposed regions of a coating layer of the resist less developer soluble than unexposed regions, and positive-acting resist compositions which undergo a photoacid-promoted deprotection reaction of acid labile groups of one or more composition components to render exposed regions of a coating layer of the resist more soluble in an aqueous developer than unexposed regions. Ester groups that contain a tertiary non-cyclic alkyl carbon or a tertiary alicyclic carbon covalently linked to the carboxyl oxygen of the ester are generally preferred photoacid-labile groups of resins employed in photoresists of the invention.

As discussed above, preferred imaging wavelengths of photoresists of the invention include sub-300 nm wavelengths e.g. 248 run, and sub-200 nm wavelengths e.g. 193 nm and 157 nm, and higher energy radiation such as radiation having a wavelength of less than 100 nm, and otherwise high energy radiation such as ETV, electron beam, ion beam or x-ray.

Particularly preferred photoresists of the invention contain an imaging-effective amount of one or more PAGs of the above Formulae I, II, IA, IB, IC, III, IV, IIIA, IIIB, IVA, V, VI, VA, VB, VIA, VII, VIII, IX, X, XI, XII, XIII and/or XIV and a resin that is selected from the group of:

1) a phenolic resin that contains acid-labile groups that can provide a chemically amplified positive resist particularly suitable for imaging at 248 nm. Particularly preferred resins of this class include: i) polymers that contain polymerized units of a vinyl phenol and an alkyl acrylate, where the polymerized alkyl acrylate (which includes (meth) acrylates) units can undergo a deblocking reaction in the presence of photoacid. Exemplary alkyl acrylates (which includes (meth)acrylates) that can undergo a photoacid-induced deblocking reaction include e.g. t-butyl acrylate, t-butyl methacrylate, methyladamantyl acrylate, methyl adamantyl methacrylate, and other non-cyclic alkyl and alicyclic acrylates (which includes (meth)acrylates) that can undergo a photoacid-induced reaction; such polymers have been described in U.S. Pat. Nos. 6,042,997 and 5,492,793, incorporated herein by reference; ii) polymers that contain polymerized units of a vinyl phenol, an optionally substituted vinyl phenyl (e.g. styrene) that does not contain a hydroxy or carboxy ring substituent, and an alkyl acrylate (which includes (meth)acrylates) such as those deblocking groups described with polymers i) above, such as polymers described in U.S. Pat. No. 6,042,997, incorporated herein by reference; and iii) polymers that contain repeat units that comprise an acetal or ketal moiety that will react with photoacid, and optionally aromatic repeat units such as phenyl or phenolic groups, such as polymers as described in U.S. Pat. Nos. 5,929,176 and 6,090,526, incorporated herein by reference.

2) a resin that is substantially or completely free of phenyl or other aromatic groups that can provide a chemically amplified positive resist particularly suitable for imaging at sub-200 nm wavelengths such as 193 nm. Particularly preferred resins of this class include: i) polymers that contain polymerized units of a non-aromatic cyclic olefin (endocyclic double bond) such as an optionally substituted norbornene, such as polymers described in U.S. Pat. Nos. 5,843,624 and 6,048,664, incorporated herein by reference; ii) polymers that contain alkyl acrylate units such as e.g. t-butyl acrylate, t-butyl methacrylate, methyladamantyl acrylate, methyl adamantyl methacrylate, and other non-cyclic alkyl and alicyclic acrylates; such polymers have been described in U.S. Pat. No. 6,057,083; European Published Applications EP01008913A1 and EP00930542A1; and U.S. pending patent application No. 09/143,462, filed Aug. 28, 1998, all incorporated herein by reference; and iii) polymers that contain polymerized anhydride units, particularly polymerized maleic anhydride and/or itaconic anhydride units, such as disclosed in European Published Application EP01008913A1 and U.S. Pat. No. 6,048,662, both incorporated herein by reference; and/or combinations of one or-more resins of types i), ii) or iii), i.e. combinations of one or more of polymers that polymerized units of a non-aromatic cyclic olefin, polymers that contain alkyl acrylates (which includes (meth)acrylates); and/or polymers that contain polymerized anhydride units.

Resists of the invention also may comprise a mixture of distinct PAGs, typically a mixture of 2 or 3 different PAGs, more typically a mixture that consists of a total of 2 distinct PAGs. At least one PAG of the mixture will be a compound of the invention, preferably a PAG compound of Formulae I, II, III, IV, V, VI, VII, IX, X, XI, XII, XIII or XIV. The other PAG(s) of the mixture also may be a PAG of any one of Formulae I through XIV, or may be another type of PAG, including other iodonium or sulfonium compound, or a non-ionic compound, preferably without any aromatic content such as an imidosulfonate PAG compound. Photoresists that contain such PAG mixtures can exhibit even further enhanced lithographic performance.

The invention also provide methods for forming relief images of the photoresists of the invention, including methods for forming highly resolved patterned photoresist images (e.g. a patterned line having essentially vertical sidewalls) of sub-quarter micron dimensions or less, such as sub-0.2 or sub-0.1 micron dimensions.

The invention further provides articles of manufacture comprising substrates such as a microelectronic wafer or a flat panel display substrate having coated thereon the photoresists and relief images of the invention. Other aspects of the invention are disclosed infra.

DETAILED DESCRIPTION OF THE INVENTION

As discussed above, the invention provides sulfonium and iodonium PAG compounds that have one or more cation substituents of optionally substituted naphthyl, optionally substituted thienyl and pentafluorophenyl. Preferred PAGs of the invention have a structure of Formulae I, II, IA, IB, IIA, III, IV, IIIA, IIIB, IVA, V, VI, VA, VB, VII, VIII, IX, X, XI, XII, XIII or XIV, as defined above.

As stated above, various substituent groups of PAGs of the invention may be optionally substituted. Substituted moieties (including substituted R, X, $R^1$, and $R^2$ groups of the above formulae) are suitably substituted at one or more available positions by, e.g., halogen such as F, Cl Br and/or I, nitro, cyano, sulfono, alkyl including $C_{1-6}$ alkyl with $C_{1-8}$ alkyl being preferred, haloalkyl such as fluoroalkyl (e.g. trifluoromethyl) and perhaloalkyl such as perfluoro$C_{1-4}$alkyl, alkoxy including $C_{1-6}$ alkoxy having one or more oxygen linkages with $C_{1-8}$ alkoxy being preferred, alkenyl including $C_{2-12}$ alkenyl with $C_{2-8}$ alkenyl being preferred, alkenyl including $C_{2-12}$ alkenyl with $C_{2-8}$ alkynyl being preferred, aryl such as phenyl or naphthyl and substituted aryl such as halo, alkoxy, alkenyl, alkynyl and/or alkyl substituted aryl, preferably having the number of carbon atoms mentioned above for corresponding groups. Preferred substituted aryl groups include substituted phenyl, anthracenyl and naphthyl.

As used herein, the term alkyl, alkenyl and alkynyl unless otherwise modified refers to both cyclic and noncyclic groups, although of course cyclic groups will comprise at least three carbon ring members. Alkenyl and alkynyl groups of compounds of the invention have one or more unsaturated linkages, typically 1 to about 3 or 4 unsaturated linkages. Also, the terms alkenyl and alkynyl as used herein refer to both cyclic and noncyclic groups, although straight or branched noncyclic groups are generally more preferred. Alkoxy groups of PAG compounds of the invention have one or more oxygen linkages, typically 1 to about 5 or 6 oxygen linkages. Alkylthio groups of PAGs of the invention have one or more thioether linkages, typically 1 to about 5 or 6 thioether linkages. Alkylsulfmyl groups of PAG compounds of the invention have one or more sulfinyl (SO) linkages, typically 1 to about 5 or 6 sulfinyl linkages. Alkylsulfonyl groups of PAG compounds of the invention have one or more sulfonyl ($SO_2$) linkages, typically 1 to about 5 or 6 sulfonyl linkages. Preferred alkylamino groups of PAG compounds of the invention include those groups having one or more primary, secondary and/or tertiary amine groups, preferably 1 to about 3 or 4 amine groups. Suitable alkanoyl groups have one or more carbonyl groups, typically 1 to about 4 or 5 carbonyl groups. Alkoxy, alkylthio, alkylsulfinyl, alkylsulfonyl, alkanoyl and other groups may be suitably either linear or branched. Carbocyclic aryl as used herein refers to non-hetero aromatic groups that have 1 to 3 separate or fused rings and 6 to about 18 carbon ring members and may include e.g. phenyl, naphthyl, biphenyl, acenaphthyl, phenanthracyl, and the like. Phenyl and naphthyl are often preferred. Suitable heteroaromatic or heteroaryl groups will have 1 to 3 rings, 3 to 8 ring members in each ring and from 1 to about 3 hetero atoms (N, O or S). Specifically suitable heteroaromatic or heteroaryl groups include e.g. courmarinyl, quinolinyl, pyridyl, pyrazinyl, pyrimdinyl, furyl, pyrrolyl, thienyl, thiazolyl, oxazolyl, imidazolyl, indolyl, benzofuranyl, benzothiophene and benzothiazole.

PAGs of the invention can be readily prepared by known methods. More particularly, sulfonium PAGs of the invention can be prepared e.g. by Grignard reaction with a substituted sulfoxide compound. Thus, for instance, to prepare a tri-naphthyl sulfonium compound, of an optionally substituted naphthyl Grignard reagent, such as naphthyl magnesium chloride can be reacted with a di-naphthyl sulfoxide (where the naphthyl groups are the same or different). Iodonium compounds of the invention can be suitably prepared e.g. by methods disclosed in U.S. Pat. No. 5,879,856, Example 2 thereof. Thus, an iodonium PAG of the invention can be prepared by reaction of a mixture of an iodate such as potassium iodate, with a thienyl, naphthyl or pentafluorophenyl compound and acetic anhydride with sulfuric acid added suitably dropwise to the mixture, preferably at reduced temperatures such as provided by ice-bath cooling. Other compounds can be reacted to provide other substituents of the iodonium compound. The reaction mixture then can be suitably stirred at room temperature until substantial reaction completion to provide the desired cation. The mixture then can be cooled, e.g. to ca. 5–10° C., and then the anion component is added, e.g. a substituted sulfonic or carboxylic acid, followed by neutralization with suitable base such as ammonium hydroxide. To prepare iodonium PAG compounds having a thienyl substituent, synthetic methods can be employed as generally described in Beringer et al., *Journal of Organic Chemistry*, 35(16):2095 (1970). To prepare iodonium PAG compounds having one or more naphthyl substituents, synthetic methods can be employed as generally described in Beringer et al., *Journal of Organic Chemistry*, 34(3):685 (1969). To prepare sulfonium PAGs of the invention where the sulfonium cation is a ring member (see Formulae XIII and XIV above), the sulfur ring compound such as thiophene or thianaphthene can be reacted with another addition group in the presence of copper benzoate. See generally Examples 1 through 5 which follow for preferred syntheses.

As discussed above, PAGs of the invention' are useful as the radiation sensitive component in photoresist compositions, including both positive-acting and negative-acting chemically amplified resist compositions.

The photoresists of the invention typically comprise a resin binder and a photoactive component of the invention as described above. Preferably the resin binder has functional groups that impart alkaline aqueous developability to the resist composition. For example, preferred are resin binders that comprise polar functional groups such as hydroxyl or carboxylate. Preferably the resin binder is used in a resist composition in an amount sufficient to render the resist developable with an aqueous alkaline solution.

For imaging at wavelengths greater than 200 nm, such as 248 nm, phenolic resins are typically preferred. Preferred phenolic resins are poly (vinylphenols) which may be formed by block polymerization, emulsion polymerization or solution polymerization of the corresponding monomers in the presence of a catalyst. Vinylphenols useful for the production of polyvinyl phenol resins may be prepared, for example, by hydrolysis of commercially available coumarin or substituted coumarin, followed by decarboxylation of the resulting hydroxy cinnamic acids. Useful vinylphenols may also be prepared by dehydration of the corresponding hydroxy alkyl phenols or by decarboxylation of hydroxy cinnamic acids resulting from the reaction of substituted or nonsubstituted hydroxybenzaldehydes with malonic acid. Preferred polyvinylphenol resins prepared from such vinylphenols have a molecular weight range of from about 2,000 to about 60,000 daltons.

Copolymers containing phenol and nonaromatic cyclic alcohol units also are preferred resin binders for resists of the invention and may be suitably prepared by partial hydrogenation of a novolak or poly(vinylphenol) resin. Such copolymers and the use thereof in photoresist compositions are disclosed in U.S. Pat. No. 5,128,232 to Thackeray et al.

Additional suitable resins include those formed from bishydroxymethylated compounds, and block novolak resins. See U.S. Pat. Nos. 5,130,410 and 5,128,230 where such resins and use of same in photoresist compositions is disclosed. Additionally, two or more resin binders of similar or different compositions can be blended or combined together to give additive control of lithographic properties of a photoresist composition. For instance, blends of resins can be used to adjust photospeed and thermal properties and to control dissolution behavior of a resist in a developer.

Preferably, a photoacid generator compound of the invention is employed in a chemically amplified positive-acting resist. A number of such resist compositions have been described, e.g., in U.S. Pat. Nos. 4,968,581; 4,883,740; 4,810,613 and 4,491,628 and Canadian Patent Application 2,001,384, all of which are incorporated herein by reference for their teaching of making and using chemically amplified positive-acting resists. In accordance with the present invention, those prior resist compositions are modified by substitution of the photoactive component of the invention as the radiation sensitive component.

For imaging at wavelengths greater than 200 nm, such as 248 nm, a particularly preferred chemically amplified photoresist of the invention comprises in admixture a photoactive component of the invention and a resin binder that comprises a copolymer containing both phenolic and non-phenolic units. For example, one preferred group of such copolymers has acid labile groups substantially, essentially or completely only on non-phenolic units of the copolymer, particularly alkylacrylate photoacid-labile groups, i.e.,a phenolic-alkyl acrylate copolymer. One especially preferred copolymer binder has repeating units x and y of the following formula:

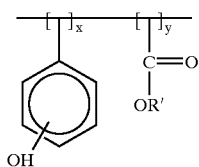

wherein the hydroxyl group be present at either the ortho, meta or para positions throughout the copolymer, and R' is substituted or unsubstituted alkyl having 1 to about 18 carbon atoms, more typically 1 to about 6 to 8 carbon atoms. Tert-butyl is a generally preferred R' group. An R' group may be optionally substituted by e.g. one or more halogen particularly F, Cl or Br), $C_{1-8}$ alkoxy, $C_{2-8}$ alkenyl, etc. The units x and y may be regularly alternating in the copolymer, or may be randomly interspersed through the polymer. Such copolymers can be readily formed. For example, for resins of the above formula, vinyl phenols and a substituted or unsubstituted alkyl acrylate such as t-butylacrylate and the like may be condensed under free radical conditions as known in the art. The substituted ester moiety, i.e. R'—O—C(=O)—, moiety of the acrylate units serves as the acid labile groups of the resin and will undergo photoacid induced cleavage upon exposure of a coating layer of a photoresist containing the resin. Preferably the copolymer will have a $M_w$ of from about 8,000 to about 50,000, more preferably about 15,000 to about 30,000 with a molecular weight distribution of about 3 or less, more preferably a molecular weight distribution of about 2 or less. Non-phenolic resins, e.g. a copolymer of an alkyl acrylate such as t-butylacrylate or t-butylmethacrylate and a vinyl alicyclic such as a vinyl norbornanyl or vinyl cyclohexanol compound, also may be used as a resin binder in compositions of the invention. Such copolymers also may be prepared by such free radical polymerization or other known procedures and suitably will have a $M_w$ of from about 8,000 to about 50,000, and a molecular weight distribution of about 3 or less.

Another preferred resin binder for a positive chemically amplified resist of the invention has phenolic and nonaromatic cyclic alcohol units, wherein at least of portion of the hydroxyl groups of the copolymer are bonded to acid labile groups. Preferred acid labile moieties are acetate groups including t-butyl acetate groups of the formula $(CH_3)_3COC(O)CH_2$—; oxycarbonyl groups such as t-butyl oxycarbonyl (t-Boc) groups of the formula $(CH_3)_3CC(O)O$—; and acetal and ketals. Chemically amplified positive-acting photoresists containing such a copolymer have been disclosed in U.S. Pat. No. 5,258,257 to Sinta et al.

Other preferred resins that have acid-labile deblocking groups for use in a positive-acting chemically-amplified photoresist of the invention have been disclosed in European Patent Application 0829766A2 of the Shipley Company (resins with acetal and ketal resins) and European Patent Application EP0783136A2 of the Shipley Company (terpolymers and other copolymers including units of 1) styrene; 2) hydroxystyrene; and 3) acid labile groups, particularly alkyl acrylate acid labile groups such as t-butylacrylate or t-butylmethacrylate). In general, resins having a variety of acid labile groups will be suitable, such as acid sensitive esters, carbonates, ethers, imides, etc. The photoacid labile groups will more typically be pendant from a polymer backbone, although resins that have acid labile groups that are integral to the polymer backbone also may be employed.

PAGs of the invention also are preferably used with polymers that contain one or more photoacid-labile groups and that are substantially, essentially or completely free of phenyl or other aromatic groups. Such photoresist compositions are particularly useful for imaging with sub-200 nm radiation such as 193 nm radiation.

For example, preferred polymers contain less than about 5 mole percent aromatic groups, more preferably less than about 1 or 2 mole percent aromatic groups, more preferably less than about 0.1, 0.02, 0.04 and 0.08 mole percent aromatic groups and still more preferably less than about 0.01 mole percent aromatic groups. Particularly preferred polymers are completely free of aromatic groups. Aromatic groups can be highly absorbing of sub-200 nm radiation and thus are undesirable for polymers used in photoresists imaged with such short wavelength radiation.

Suitable polymers that are substantially or completely free of aromatic groups and may be formulated with a PAG of the invention to provide a photoresist for sub-200 nm imaging are disclosed in European application EP930542A1 of the Shipley Company.

Suitable polymers that are substantially or completely free of aromatic groups suitably contain acrylate units such as photoacid-labile acrylate units as may be provided by polymerization of methyladamantylacrylate, methyladamantylmethacrylate, ethylfenchylacrylate, ethylfenchylmethacrylate, and the like; fused non-aromatic alicyclic groups such as may be provided by polymerization of a norbornene compound or other alicyclic compound having an endocyclic carbon-carbon double bond; an anhydride such as may be provided by polymerization of maleic anhydride; and the like.

Preferred negative-acting compositions of the invention comprise a mixture of materials that will cure, crosslink or harden upon exposure to acid, and a photoactive component of the invention.

Particularly preferred negative acting compositions comprise a resin binder such as a phenolic resin, a crosslinker component and a photoactive component of the invention. Such compositions and the use thereof has been disclosed in European Patent Applications 0164248 and 0232972 and in U.S. Pat. No. 5,128,232 to Thackeray et al. Preferred phenolic resins for use as the resin binder component include novolaks and poly(vinylphenol)s such as those discussed above. Preferred crosslinkers include amine-based materials, including melamine, glycolurils, benzoguanamine-based materials and urea-based materials. Melamine-formaldehyde resins are generally most preferred. Such crosslinkers are commercially available, e.g. the melamine resins sold by American Cyanamid under the trade names Cymel 300, 301 and 303. Glycoluril resins are sold by American Cyanamid under trade names Cymel 1170, 1171, 1172, urea-based resins are sold under the trade names of Beetle 60, 65 and 80, and benzoguanamine resins aresold under the trade names Cymel 1123 and 1125.

Photoresists of the invention also may contain other materials. For example, other optional additives include actinic and contrast dyes, anti-striation agents, plasticizers, speed enhancers, sensitizers (e.g. for use of a PAG of the invention at longer wavelengths such as I-line (i.e. 365 nm) or G-line wavelengths), etc. Such optional additives typically will be present in-minor concentration in a photoresist composition except for fillers and dyes which may be present in relatively large concentrations such as, e.g., in amounts of from 5 to 30 percent by weight of the total weight of a resist's dry components.

A preferred optional additive of resists of the invention is an added base, particularly tetrabutylammonium hydroxide (TBAH), which can enhance resolution of a developed resist relief image. The added base is suitably used in relatively small amounts, e.g. about 1 to 10 percent by weight relative to the PAG, more typically 1 to about 5 weight percent. Other preferred basic additives include ammonium sulfonate salts such as piperidinium p-toluenesulfonate and dicyclohexylammonium p-toluenesulfonate; alkyl amines such as tripropylamine and dodecylamine; aryl amines such as diphenylamine, triphenylamine, aminophenol, 2-(4-aminophenyl)-2-(4-hydroxyphenyl)propane, etc.

The resin binder component of resists of the invention are typically used in an amount sufficient to render an exposed coating layer of the resist developable such as with an aqueous alkaline solution. More particularly, a resin binder will suitably comprise 50 to about 90 weight percent of total solids of the resist. The photoactive component should be present in an amount sufficient to enable generation of a latent image in a coating layer of the resist. More specifically, the photoactive component will suitably be present in an amount of from about 1 to 40 weight percent of total solids of a resist. Typically, lesser amounts of the photoactive component will be suitable for chemically amplified resists.

The photoresists of the invention are generally prepared following known procedures with the exception that a PAG of the invention is substituted for prior photoactive compounds used in the formulation of such photoresists. For example, a resist of the invention can be prepared as a coating composition by dissolving the components of the photoresist in a suitable solvent such as, e.g., a glycol ether such as 2-methoxyethyl ether (diglyme), ethylene glycol monomethyl ether, propylene glycol monomethyl ether and propylene glycol monomethyl ether acetate; lactates such as ethyl lactate or methyl lactate, with ethyl lactate being preferred; propionates, particularly methyl propionate, ethyl propionate and 3-ethyl ethoxypropionate; a Cellosolve ester such as methyl Cellosolve acetate; an aromatic hydrocarbon such toluene or xylene; or a ketone such as methylethyl ketone, cyclohexanone and 2-heptanone. Typically the solids content of the photoresist varies between 5 and 35 percent by weight of the total weight of the photoresist composition.

The photoresists of the invention can be used in accordance with known procedures. Photoresists of the invention are preferably applied on a substrate as a liquid coating composition, dried by heating to remove solvent preferably until the coating layer is tack free, exposed through a photomask to activating radiation, optionally post-exposure baked to create or enhance solubility differences between exposed and nonexposed regions of the resist coating layer, and then developed preferably with an aqueous alkaline developer to form a relief image.

The substrate on which a resist of the invention. is applied and processed suitably can be any substrate used in processes involving photoresists such as a microelectronic wafer. For example, the substrate can be a silicon, silicon dioxide or aluminum-aluminum oxide microelectronic wafer. Gallium arsenide, ceramic, quartz or copper substrates may also be employed. Printed circuit board substrates such as copper clad laminates are also particularly preferred. The photoresists of the invention will be particularly useful for circuit board imaging, including through hole and other aperture plating. Typical printed circuit board substrates have one or more copper layers interleaved with resin layers, such as epoxy layers.

Substrates used for liquid crystal display and other flat panel display applications are also suitably employed, e.g. glass substrates, indium tin oxide coated substrates and the like.

A liquid coating resist composition may be applied by any standard means such as spinning, dipping or roller coating. Photoresists of the invention also may be formulated and applied as dry film resists, particularly for printed circuit board manufacture applications. The exposure energy should be sufficient to effectively activate the photoactive component of the radiation sensitive system to produce a patterned image in the resist coating layer. Suitable exposure energies typically range from about 1 to 300 mJ/cm$^2$. As discussed above, preferred exposure wavelengths include sub-300 nm such as 248 nm, and sub-200 nm and sub-160 nm such as 193 nm and 157 nm. Higher energy exposure sources also may be employed such as EUV, electron beam, ion beam and x-ray radiation, and other ionizing radiation. Suitable post-exposure bake temperatures are from about 50° C. or greater, more specifically from about 50 to 150° C. For an acid-hardening negative-acting resist, a post-development bake may be employed if desired at temperatures of from about 100 to 150° C. for several minutes or longer to further cure the relief image formed upon development. After development and any post-development cure, the substrate surface bared by development may then be selectively processed, for example chemically etching or plating substrate areas bared of photoresist in accordance with procedures known in the art. Suitable etchants include a hydrofluoric acid etching solution and a plasma gas etch such as an oxygen plasma etch.

All documents mentioned herein are incorporated herein by reference. The following non-limiting example is illustrative of the invention.

EXAMPLE 1–5

Syntheses of Photoacid Generator Compounds

EXAMPLE 1

Preparation of di(1-Naphthyl)phenylsulfonium Triflate

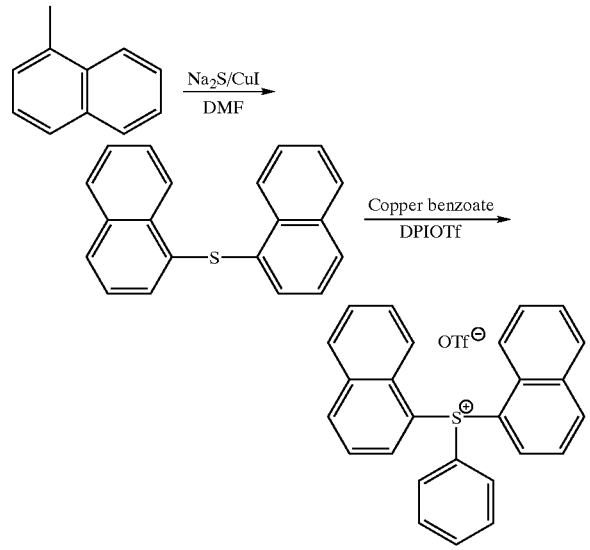

Under a nitrogen atmosphere, anhydrous sodium sulfide (4.3 g, 0.055 mole) and CuI (1.9 g, 0.010 mole) is added to a solution of 1-iodonaphthalene (27.9 g, 0.110 mole) in 100 ml dry THF and the solution is refluxed for 24 h. After cooling, 500 ml water is added and the mixture extracted three times with dichloromethane (100 ml). The combined organic phases are washed with 2N NaOH (3×50 mL), dried and the solvent is removed. The brownish-yellow crude product is purified by column chromatography on silica gel (ethylacetate/cyclohexane 1:4), yielding 6 g (30%) of the sulfide as a white solid. The structure was confirmed by $^1$H/$^{13}$C NMR spectroscopy.

Di(1-naphthyl)sulfide (3 g, 0.0104 mole), diphenyliodonium triflate (5.8 g, 0.0135 mole) and copper benzoate (0.08 g, 0.003 mole) are heated without solvent for 3 hours at 120–145° C. under a nitrogen atmosphere. After cooling down, 75 ml ether was added and the mixture vigorously stirred overnight to achive solidification. Filtration and washing with ether yielded a brown solid, which was dissolved in hot water, the solution filtered and the water removed in vacuo. The resulting white solid was stirred in 50 ml ethyl ether for 24 hours, the mixture filtered and the residue washed with ethyl ether, yielding 4.8 g (90%) of the title compound, di-(1-naphthyl)phenylsulfonium triflate. The structure was confirmed by $^1H/^{13}C$ NMR spectroscopy.

EXAMPLE 2

Preparation of (2-Thienyl)diphenylsulfonium Triflate

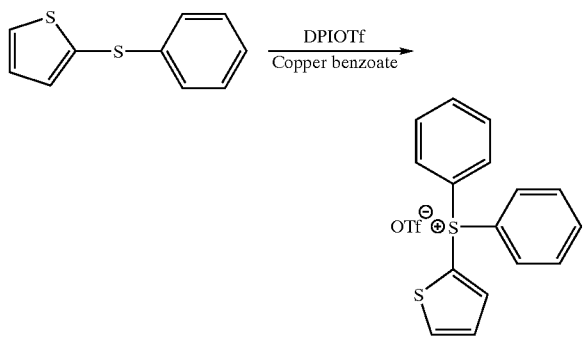

EXAMPLE 3

Preparation of di-(2-Thienyl)phenylsulfonium Triflate

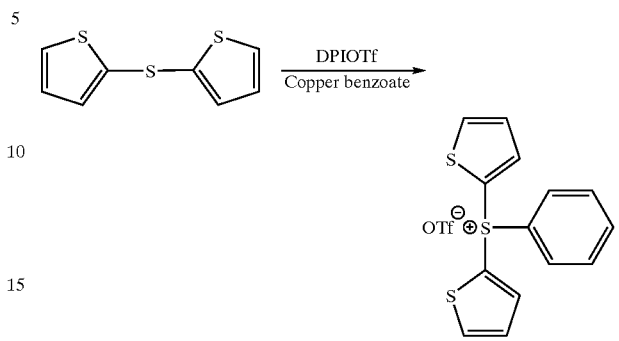

Di-(2-thienyl)sulfide (2.1 g, 0.0104 mole), diphenyliodonium triflate (5.8 g, 0.0135 mole) and copper benzoate (0.08 g, 0.003 mole) are heated without solvent for 3 hours at 120–145° C. under a nitrogen atmosphere. After cooling down, 75 ml ethyl ether was added and the mixture vigorously stirred overnight to achieve solidification. Filtration and washing with ethyl ether yielded a brown solid, which was dissolved in hot water, the solution filtered and the water removed in vacuo. The resulting white solid was stirred in 50 ml ethyl ether for 24 hours, the mixture filtered and the residue washed with ethyl ether, yielding 3.4 g (78%) of the title compound, di(2-thienyl)phenylsulfonium triflate. The structure was confirmed by $^1H/^{13}C$ NMR spectroscopy.

EXAMPLE 4

Preparation of di(Pentafluorophenyl) phenylsulfonium Triflate

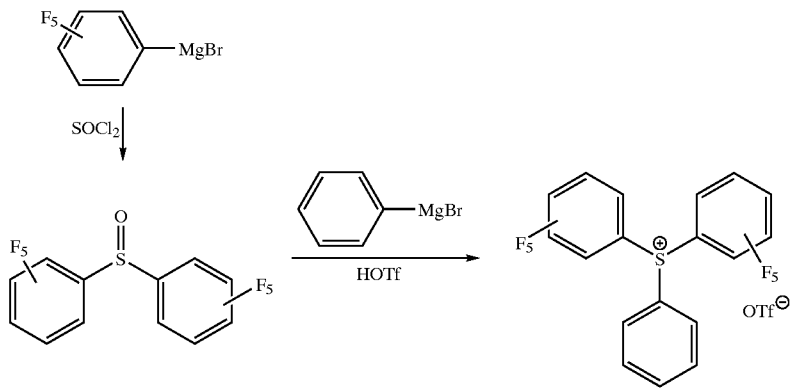

(2-thienyl)phenylsulfide (2.0 g, 0.0104 mole), diphenyliodonium triflate (5.8 g, 0.0135 mole) and copper benzoate (0.08 g, 0.003 mole) are heated without solvent for 3 hours at 120–145° C. under nitrogen atmosphere. After cooling down, 75 ml ethyl ether was added and the mixture vigorously stirred overnight to achieve solidification. Filtration and washing with ethyl ether yielded a brown solid, which was dissolved in hot water, the solution filtered and the water removed in vacuo. The resulting white solid was stirred in 50 ml ether for 24 hours, the mixture filtered and the residue washed with ethyl ether, yielding 3.9 g (90%) of the title compound, (2-thienyl)diphenylsulfonium triflate. The structure was confirmed by $^1H/^{13}C$ NMR.

To thionyl chloride (4 ml, 0.055 mole) in 12 ml ethyl ether is dropwise added a 0.5 M solution of pentafluorophenylmagnesium bromide in ethyl ether (100 g, 0.05 mole) at −25° C. with stirring. After the addition is complete, the mixture is allowed to warm to room temperature and the stirring is continued for 1 hour. The mixture is filtered, washed with water twice, dried over magnesium sulfate and the solvent removed in vacuo, yielding a brown solid. The residue from the filtration is dissolved in ethyl ether/water again, the phases are separated and the ethyl ether layer washed with water twice, dried over magnesium sulfate and the solvent removed in vacuo, yielding more crude product. The purification was done by sublimation and subsequent recrysallization from cyclohexane, yielding 6.9 g (72%), of the sulfoxide as a white solid.

A 3M solution of phenylmagnesium bromide in ether (17 ml, 0.05 mole) is heated slowly to 80° C. under vacuum to remove the ether. 8 ml benzene and 17 ml heptane were then added and subsequently pentafluorophenyl sulfoxide (3.8 g, 0.01 mole), dissolved in 15 ml benzene, was added dropwise at 80° C. over one hour. After stirring for three hours, the solution is allowed to cool to room temperature, followed by the addition of 33 ml of 25% triflic acid. The organic layer was separated and extracted twice with 10 ml of 5% triflic acid. The aqueous layers were combined and extracted three times with 100 ml diclhoromethane and solvent removed after drying over magnesium sulfate, yielding 600 mg (10%) of di(pentafluorophenyl)phenyl sulfonium triflate. The structure was confirmed by $^1H/^{13}C$ NMR.

EXAMPLE 5

Preparation of 1-Phenyl-2-methylbenzothiophenium Triflate

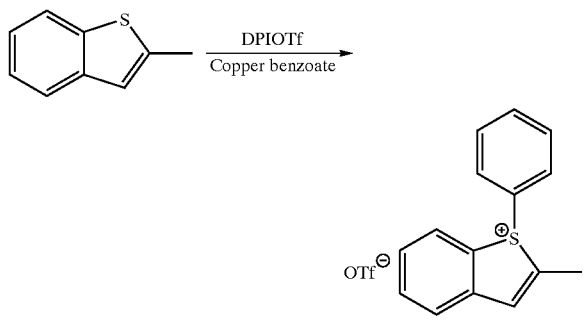

2-Methylthianaphthene (5 g, 0.0327 mole), diphenyliodonium triflate (18.28 g, 0.0425 mole) and copper benzoate (0.1 g, 0.000327 mole) were heated without solvent for 0.5 hours at 140° C. under a nitrogen atmosphere. After cooling down, 150 ethyl ether was added to solidify the product. Filtration and washing with ethyl ether yielded a brownish-grey solid, which was dissolved in 500 ml hot water, and the solution filtered and the water removed in vacuo. The resulting off-white solid was stirred in 50 ml ethyl ether for 1 hour, the mixture filtered and the residue washed with ethyl ether. The product was recrystallized from dichloromethane/t-butyl methyl ether to yield 8.97 g (76%) of 1-phenyl-2-methylbenzothiophenium triflate. The structure was confirmed by $^1H/^{13}C$ NMR spectroscopy.

EXAMPLES 6–8

Photoresist Preparation and Lithographic Processing

EXAMPLE 6

Photoresist Preparation and Lithographic Processing

A photoresist of the invention is prepared by mixing the following components with amounts expressed as weight percent based on total weight of the resist compositions:

| Resist components | Amount (wt. %) |
|---|---|
| Resin binder | 15 |
| Photoacid generator | 3 |
| Ethyl lactate | 81 |

The resin binder is a terpolymer consisting of polymerized 60 mole percent vinylphenol units, 20 mole percent styrene units and 20 mole percent t-butylacrylate. The photoacid generator was the compound di(1-naphthyl)phenylsulfonium triflate, as prepared in Example 1 above. Those resin and PAG components are admixed in the ethyl lactate solvent.

The formulated resist composition is spin coated onto HMDS vapor primed 4 inch silicon wafers and softbaked via a vacuum hotplate at 90° C. for 60 seconds. The resist coating layer is exposed through a photomask at 248 nm, and then the exposed coating layers are post-exposure baked at 110° C. The coated wafers are then treated with 0.26N aqueous tetrabutylammonium hydroxide solution to develop the imaged resist layer and provide a relief image.

EXAMPLE 7

A resist formulation was prepared that contained in admixture: a copolymer of 2-methyl-2-adamantyl methacrylate and 3-methacrolyl butyrolactone (30 g of a 30 wt. % solution in 2-heptanone); di(2-thienyl)phenylsulfonium triflate (0.167 g); triisopropanolamine (0.48 g of a 1 wt. % solution in 2-heptanone); a siloxane surfactant (0.48 g of a 1 wt. % solution in 2-heptanone); and 13.27 g of 2-heptanone. The resulting solution was spin coated on a Polaris system onto silicon wafers (150 mm) over a crosslinked organic antireflective coating layer (820 angstrom antireflective layer thickness). The coated wafer was baked (proximity) at 120° C. for 60 seconds to form a resist film having a thickness of 3900+/−25 angstroms. The resulting wafers were exposed using a LOGIC reticle on an ISI microstepper under conventional illumination conditions. The wafers were post-exposure baked at 120° C. for 60 seconds then developed in 0.26N tetramethyl ammonium hydroxide aqueous developer using a 60 second single puddle process. Development yielded 120 nm 1:1 dense line features.

EXAMPLE 8

A positive working photoresist formulation was prepared that contained: 11.0 g each of two terpolymers of p-hydroxystyrene, m-hydroxystyrene, and methyl adamantylmethacrylate (each 25 wt. % solution in propylene glycol monomethyl ether acetate (PMA)); 0.19 g of 1-phenyl-2-methylbenzothiophenium triflate; an tetraalkyl ammonium hydroxide salt (5.50 g of a 1 wt. % solution in PMA); a siloxane surfactant (0.61 g of a 10 wt. % solution in ethyl lactate); 7.59 g ethyl lactate; and 10.59 g PMA. The resulting solution was filtered through a 0.20 μm membrane and then spin coated on a TEL Mark8 system onto silicon wafers (150 mm) over a crosslinked organic antireflective coating layer (600 angstrom antireflective layer thickness). The coated wafer was baked (proximity) at 130° C. for 60 seconds to form a resist film having a thickness of 4150+/−25 angstroms. The resulting wafers were exposed at 248 nm using a GCA XLS 7800 0.53 NA (0.74σ) stepper using conventional illumination. The wafers were post-exposure baked at 130° C. for 90 seconds then developed in 0.26N tetramethyl ammonium hydroxide aqueous developer using a 30 second single puddle process. Development yielded 180 nm 1:1 dense line features.

The foregoing description of the invention is merely illustrative thereof, and it is understood that variations and modifications can be effected without departing from the spirit or scope of the invention as set forth in the following claims.

What is claimed is:

1. A method for forming a photoresist relief image on a substrate comprising:

(a) applying a coating layer of chemically-amplified positive photoresist composition on a substrate, the photoresist composition comprising a resin and an iodonium or sulfonium photoacid generator compound which has one or more cation substituents selected from the group consisting of optionally substituted naphthyl, optionally substituted thienyl and pentafluorophenyl; and (b) exposing the photoresist coating layer to patterned activating radiation having a wavelength of less than about 160 nm and developing the exposed photoresist layer.

2. The method of claim 1 wherein the photoacid generator compound is a sulfonium compound.

3. The method of claim 2 wherein the sulfur cation is a ring member.

4. The method of claim 1 wherein the photoacid generator is an idonium compound.

5. The method of claim 1 wherein the photoacid generator compound comprises an optionally substituted naphthyl moiety on the cation.

6. The method of claim 1 wherein the photoacid generator compound comprises an optionally substituted thienyl moiety on the cation.

7. The method of claim 1 wherein the photoacid generator compound comprises a pentafluorophenyl moiety on the cation.

8. The method of claim 1 wherein the photoacid generator compound comprises a carboxylate anion.

9. The method of claim 1 wherein the photoacid generator comprises a sulfonate anion.

10. The method of claim 1 wherein the photoresist is a chemically-amplified positive-acting photoresist.

11. A method for forming a photoresist relief image on a substrate comprising:

(a) applying a coating layer of chemically-amplified positive photoresist composition on a substrate, the photoresist composition comprising a resin and an iodonium or sulfonium photoacid generator compound which has a pentafluorophenyl cation substituent; and (b) exposing the photoresist coating layer to patterned activating radiation and developing the exposed photoresist layer.

12. The method of claim 11 wherein the photoacid generator compound is a sulfonium compound.

13. The method of claim 12 wherein the sulfur cation is a ring member.

14. The method of claim 11 wherein the photoacid generator is an iodonium compound.

15. The method of claim 11 wherein the photoacid generator compound comprises a carboxylate anion.

16. The method of claim 11 wherein the photoacid generator compound comprises a sulfonate anion.

17. The method of claim 11 wherein the photoresist is a chemically-amplified positive-acting photoresist.

18. The method of claim 11 wherein the photoresist coating layer is exposed to radiation having a wavelength of less than about 200 nm.

19. The method of claim 11 wherein the photoresist coating layer is exposed to radiation having a wavelength of about 193 nm.

20. A photoresist composition comprising a resin and an iodonium or sulfonium photoacid generator compound which has one or more cation substituents that is a pentafluorophenyl group.

21. The photoresist composition of claim 20 wherein the resin contains phenolic and photoacid-labile alkyl acrylate groups.

22. The photoresist composition of claim 20 wherein the resin contains 1) phenolic units, 2) phenyl groups that do not have hydroxy or carboxy ring substituents, and 3) photoacid-labile alkyl acrylate units.

23. The photoresist composition of claim 20 wherein the resin comprises acetal or ketal group.

24. The photoresist composition of claim 20 wherein the photoresist is essentially free of polymers containing aromatic units.

25. The photoresist composition of claim 20 wherein the composition is a chemically-amplified positive-acting photoresist.

26. The photoresist composition of claim 20 wherein the composition is a negative-acting-photoresist.

* * * * *